(12) United States Patent
Ryan

(10) Patent No.: US 10,945,882 B2
(45) Date of Patent: *Mar. 16, 2021

(54) SMALL GAUGE SURGICAL INSTRUMENT WITH ADJUSTABLE SUPPORT

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,306

(22) Filed: Feb. 28, 2020

(65) Prior Publication Data
US 2020/0197217 A1 Jun. 25, 2020

Related U.S. Application Data

(63) Continuation of application No. 13/628,806, filed on Sep. 27, 2012, now Pat. No. 10,617,560.

(60) Provisional application No. 61/539,655, filed on Sep. 27, 2011.

(51) Int. Cl.
A61B 1/005 (2006.01)
A61B 1/07 (2006.01)
A61F 9/007 (2006.01)

(52) U.S. Cl.
CPC ............ *A61F 9/007* (2013.01); *A61B 1/0051* (2013.01); *A61B 1/07* (2013.01); *A61F 9/00736* (2013.01); *A61B 1/005* (2013.01); *A61B 1/0052* (2013.01)

(58) Field of Classification Search
CPC ... A61B 1/0052; A61B 1/00064; A61F 9/007; A61F 9/00736; A61F 9/781; A61F 9/013; A61F 9/008; A61F 2009/00874; A61F 2/1664; A61F 2/167; A61F 2/1672; A61M 2210/0612
See application file for complete search history.

(56) References Cited

U.S. PATENT DOCUMENTS

| 3,552,384 A | 1/1971 | Pierie et al. |
| 4,256,119 A | 3/1981 | Gauthier |
| 4,607,622 A | 8/1986 | Fritch et al. |
| 4,630,616 A | 12/1986 | Tretinyak |
| 4,674,497 A | 6/1987 | Ogasawara |
| 4,799,496 A | 1/1989 | Hargreaves et al. |
| 4,817,631 A | 4/1989 | Schnepp-Pesch et al. |

(Continued)

FOREIGN PATENT DOCUMENTS

| AU | 2012315978 B2 | 4/2017 |
| CA | 2850327 C | 10/2018 |

(Continued)

OTHER PUBLICATIONS

Brazilian Application Serial No. BR1120140074429, Office Action dated Jul. 20, 2020, w/o English Translation, 4 pgs.

(Continued)

Primary Examiner — Timothy J Neal
Assistant Examiner — William B Chou
(74) Attorney, Agent, or Firm — Schwegman Lundberg & Woessner, P.A.

(57) ABSTRACT

A small gauge surgical instrument is shown with advantages such as diminished "play" at the tip. A surgical instrument assembly is also shown with support along a length of the instrument that can be selected by the surgeon. Devices and method described provide adjustability of the instrument without protruding into a gripping surface of the instrument.

22 Claims, 3 Drawing Sheets

(56) References Cited

U.S. PATENT DOCUMENTS

| | | | |
|---|---|---|---|
| 4,950,272 | A | 8/1990 | Smirmaul |
| 5,281,214 | A | 1/1994 | Wilkins et al. |
| 5,403,324 | A | 4/1995 | Ciervo et al. |
| 5,469,524 | A | 11/1995 | Esch et al. |
| 5,632,717 | A | 5/1997 | Yoon |
| 5,682,892 | A | 11/1997 | Selder et al. |
| 5,690,619 | A | 11/1997 | Erskine |
| 5,700,275 | A | 12/1997 | Bell et al. |
| 5,741,225 | A | 4/1998 | Lax et al. |
| 5,766,164 | A | 6/1998 | Mueller et al. |
| 5,797,929 | A | 8/1998 | Andreas et al. |
| 5,904,648 | A | 5/1999 | Arndt et al. |
| 5,971,939 | A | 10/1999 | Desantis et al. |
| 6,221,029 | B1 | 4/2001 | Mathis et al. |
| 6,520,954 | B2 | 2/2003 | Ouchi |
| 6,572,608 | B1 | 6/2003 | Lee et al. |
| 6,575,989 | B1 | 6/2003 | Scheller et al. |
| 6,984,230 | B2 | 1/2006 | Scheller et al. |
| 7,892,282 | B2 | 2/2011 | Shepherd |
| 10,617,560 | B2 | 4/2020 | Ryan |
| 2003/0120305 | A1 | 6/2003 | Jud et al. |
| 2003/0191461 | A1 | 10/2003 | Scheller et al. |
| 2005/0003309 | A1 | 1/2005 | Cho et al. |
| 2005/0033309 | A1 | 2/2005 | Ryan |
| 2007/0129732 | A1 | 6/2007 | Zacharias |
| 2008/0255578 | A1 | 10/2008 | Neusidl |
| 2009/0272786 | A1 | 11/2009 | Zeiner et al. |
| 2012/0042471 | A1 | 2/2012 | Spiggle |
| 2013/0053759 | A1 | 2/2013 | Mccawley |
| 2013/0090531 | A1 | 4/2013 | Ryan |

FOREIGN PATENT DOCUMENTS

| | | | |
|---|---|---|---|
| CN | 101616648 | A | 12/2009 |
| CN | 103957849 | A | 7/2014 |
| CN | 103957849 | B | 3/2017 |
| DE | 3905734 | A1 | 8/1990 |
| EP | 2760400 | B1 | 1/2018 |
| IN | 2955DELNP2014 | A | 3/2015 |
| JP | 619851 | B2 | 3/1986 |
| JP | 10502566 | A | 3/1998 |
| JP | 2006522648 | A | 10/2006 |
| JP | 2009225989 | A | 10/2009 |
| JP | 6140169 | B2 | 5/2017 |
| WO | WO-2009061194 | A1 | 5/2009 |
| WO | WO-2013049341 | A2 | 4/2013 |
| WO | WO-2013049341 | A3 | 4/2013 |

OTHER PUBLICATIONS

Indian Application Serial No. 2955/DELNP/2014, Response filed Jul. 31, 2020 to First Examination Report dated Feb. 12, 2020, 13 pgs.

"U.S. Appl. No. 13/628,806, Advisory Action dated Jan. 7, 2019", 2 pgs.

"U.S. Appl. No. 13/628,806, Advisory Action dated Sep. 9, 2014", 4 pgs.

"U.S. Appl. No. 13/628,806, Amendment and Response to Non-Final Office Action filed Mar. 17, 2017", 7 pgs.

"U.S. Appl. No. 13/628,806, Decision on Pre-Appeal Brief mailed Oct. 12, 2017", 2 pgs.

"U.S. Appl. No. 13/628,806, Examiner Interview Summary dated Aug. 6, 2019", 3 pgs.

"U.S. Appl. No. 13/628,806, Final Office Action dated Apr. 1, 2015", 8 pgs.

"U.S. Appl. No. 13/628,806, Final Office Action dated Apr. 22, 2016", 9 pgs.

"U.S. Appl. No. 13/628,806, Final Office Action dated Jun. 3, 2014", 9 pgs.

"U.S. Appl. No. 13/628,806, Final Office Action dated Jul. 6, 2017", 11 pgs.

"U.S. Appl. No. 13/628,806, Final Office Action dated Sep. 26, 2018", 13 pgs.

"U.S. Appl. No. 13/628,806, Non Final Office Action dated Jan. 26, 2018", 8 pgs.

"U.S. Appl. No. 13/628,806, Non Final Office Action dated Feb. 26, 2014", 12 pgs.

"U.S. Appl. No. 13/628,806, Non Final Office Action dated Apr. 19, 2019", 14 pgs.

"U.S. Appl. No. 13/628,806, Non Final Office Action dated Oct. 6, 2015", 9 pgs.

"U.S. Appl. No. 13/628,806, Non Final Office Action dated Nov. 4, 2014", 10 pgs.

"U.S. Appl. No. 13/628,806, Non Final Office Action dated Nov. 17, 2016", 8 pgs.

"U.S. Appl. No. 13/628,806, Notice of Allowance dated Nov. 20, 2019", 7 pgs.

"U.S. Appl. No. 13/628,806, Pre-Appeal Brief filed Aug. 28, 2017", 5 pgs.

"U.S. Appl. No. 13/628,806, Response filed Jan. 6, 2016 to Non Final Office Action dated Oct. 6, 2015", 7 pgs.

"U.S. Appl. No. 13/628,806, Response filed Feb. 4, 2015 to Non Final Office Action dated Nov. 4, 2014", 5 pgs.

"U.S. Appl. No. 13/628,806, Response filed May 27, 2014 to Non Final Office Action dated Feb. 26, 2014", 6 pgs.

"U.S. Appl. No. 13/628,806, Response filed May 29, 2018 to Non Final Office Action dated Jan. 26, 2018", 8 pgs.

"U.S. Appl. No. 13/628,806, Response filed Jul. 1, 2015 to Final Office Action dated Apr. 1, 2015", 10 pgs.

"U.S. Appl. No. 13/628,806, Response filed Sep. 3, 2014 to Final Office Action dated Jun. 3, 2014", 6 pgs.

"U.S. Appl. No. 13/628,806, Response filed Oct. 3, 2014 to Final Office Action dated Jun. 3, 2014", 6 pgs.

"U.S. Appl. No. 13/628,806, Response filed Dec. 21, 2018 to Final Office Action dated Sep. 26, 2018", 8 pgs.

"U.S. Appl. No. 13/628,806, Response filed Aug. 2, 2019 to Non-Final Office Action dated Apr. 19, 2019", 8 pgs.

"U.S. Appl. No. 13/628,806, Supplemental Notice of Allowability dated Jan. 30, 2020", 2 pgs.

"U.S. Appl. No. 13/628,806, Supplemental Notice of Allowability dated Mar. 10, 2020", 2 pgs.

"Australian Application Serial No. 2012315978, First Examiner Report dated May 23, 2016", 3 pgs.

"Australian Application Serial No. 2012315978, Response filed Dec. 15, 2016 to First Examiner Report dated May 23, 2016", 11 pgs.

"Australian Application Serial No. 2012315978, Response filed Mar. 16, 2017 to Subsequent Examiners Report dated Dec. 21, 2016", 6 pgs.

"Australian Application Serial No. 2012315978, Subsequent Examiners Report dated Dec. 21, 2016", 4 pgs.

"Brazilian Application Serial No. BR1120140074429, Office Action dated Sep. 19, 2019", w/ English Translation, 8 pgs.

"Brazilian Application Serial No. BR1120140074429, Response filed Jan. 2, 2020 to Office Action dated Sep. 19, 2019", w/ English Claims, 15 pgs.

"Canadian Application Serial No. 2,850,327, Office Action dated Jun. 16, 2017", w/ English Translation, 5 pgs.

"Canadian Application Serial No. 2,850,327, Response filed Dec. 15, 2017 to Office Action dated Jun. 16, 2017", 10 pgs.

"Chinese Application Serial No. 201280058250.X, Office Action dated Mar. 25, 2015", 15 pgs.

"Chinese Application Serial No. 201280058250.X, Office Action dated Jun. 2, 2016", 9 pgs.

"Chinese Application Serial No. 201280058250.X, Office Action dated Nov. 24, 2015", w/ English Translation, 10 pgs.

"Chinese Application Serial No. 201280058250.X, Response filed Feb. 5, 2016 to Office Action dated Nov. 24, 2015", w/ English Translation of Claims, 9 pgs.

"Chinese Application Serial No. 201280058250.X, Response filed Aug. 7, 2015 to Office Action dated Mar. 25, 2015", w/ English Translation of Amended Claims, 8 pgs.

(56) References Cited

OTHER PUBLICATIONS

"Chinese Application Serial No. 201280058250.X, Response filed Aug. 15, 2016 to Office Action dated Jun. 2, 2016", w/ English translation of claims, 10 pgs.
"European Application Serial No. 12837366.9, Communication Pursuant to Article 94(3) EPC dated Oct. 27, 2016", 3 pgs.
"European Application Serial No. 12837366.9, Extended European Search Report dated May 13, 2015", 6 pgs.
"European Application Serial No. 12837366.9, Office Action dated Jun. 1, 2015", 1 pg.
"European Application Serial No. 12837366.9, Response filed Feb. 27, 2017 to Communication Pursuant to Article 94(3) EPC dated Oct. 27, 2016", 12 pgs.
"European Application Serial No. 12837366.9, Response filed Dec. 8, 2015 to Office Action dated Jun. 1, 2015", 8 pgs.
"Indian Application Serial No. 2955/DELNP/2014, First Examination Report dated Feb. 12, 2020", w/ English Translation, 6 pgs.
"International Application Serial No. PCT/US2012/057545, International Preliminary Report on Patentability dated Apr. 10, 2014", 2 pgs.
"International Application Serial No. PCT/US2012/057545, International Search Report dated Dec. 14, 2012", 2 pgs.
"International Application Serial No. PCT/US2012/057545, Written Opinion dated Dec. 14, 2012", 4 pgs.
"Japanese Application Serial No. 2014-533315, Office Action dated Jul. 12, 2016", w/ English Translation, 6 pgs.
"Japanese Application Serial No. 2014-533315, Office Action dated Nov. 29, 2016", w/ English Translation, 4 pgs.
"Japanese Application Serial No. 2014-533315, Response filed Feb. 27, 2017 to Office Action dated Nov. 29, 2016", w/ English Claims, 7 pgs.
"Japanese Application Serial No. 2014-533315, Response filed Oct. 26, 2016 to Office Action dated Jul. 12, 2016", W/ English Translation of Claims, 11 pgs.
"Machine Translation of JP 61-9851B2, published on Mar. 26, 1986", 6 pgs.
U.S. Appl. No. 13/628,806 U.S. Pat. No. 10,617,560, filed Sep. 27, 2012, Small Gauge Surgical Instrument With Adjustable Support.
"Brazilian Application Serial No. BR1120140074429, Response filed Oct. 23, 2020 to Office Action dated Jul. 20, 2020", w/ English Claims, 9 pgs.

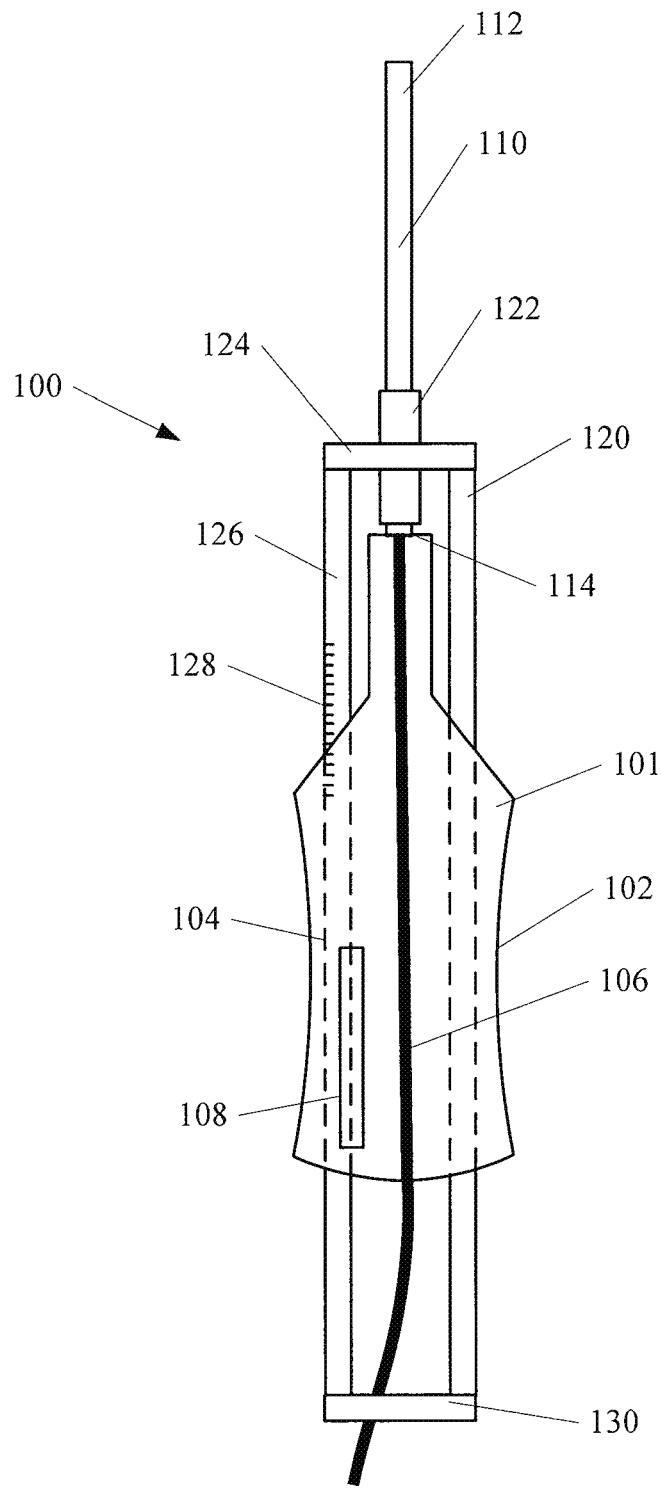
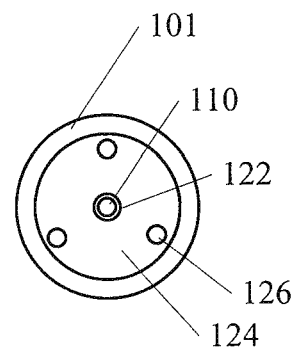
FIG. 2
FIG. 1

SMALL GAUGE SURGICAL INSTRUMENT WITH ADJUSTABLE SUPPORT

CLAIM OF PRIORITY

This patent application is a continuation of and claims the benefit of priority under 35 U.S.C. § 120 to U.S. patent application Ser. No. 13/628,806, filed on Sep. 27, 2020, which claims the benefit of priority, under 35 U.S.C. § 119(e), to U.S. Provisional Patent Application Ser. No. 61/539,655, entitled "SMALL GAUGE SURGICAL INSTRUMENT WITH ADJUSTABLE SUPPORT," filed on Sep. 27, 2011, each of which is hereby incorporated by reference herein in its entirety.

TECHNICAL FIELD

This invention relates to small gauge instruments typically used for surgical procedures such as surgery of the eye.

BACKGROUND

Ophthalmological surgery continues to evolve towards smaller instruments that produce smaller incisions. The most common incision size currently is 20 gauge (approximately 1.0 mm diameter), but newer instruments as small as 27 gauge (approximately 0.41 mm diameter) are being utilized, and smaller instruments are likely in the future. The advantages of smaller incisions are multiple, including lessened trauma, faster healing, faster wound management (no sutures), and greater patient comfort.

Problems exist with the smaller instruments, however. The small diameter of the instruments makes them quite flexible, which is a disadvantage for the surgeon. With larger diameter instruments, there is very little "play", so the tips of the instruments go exactly where the surgeon desires that they go. With the smaller diameter instruments, the tips can move from their intended positions due to the bending or flexing of the fine wire-like instruments, which makes the surgeon feel a loss of control.

Bending or flexing of the small instruments is of particular concern in some procedures, for example, removal of peripheral vitreous, when the eye must be turned to allow viewing by the surgeon. Turning of the eye is accomplished by moving the instrument relative to the patient's head while a portion of the instrument remains inserted within a portion of the eye. Because the amount of flexing of the instrument is relatively large and unpredictable to the surgeon, precise repositioning of the eye becomes more difficult. In addition, delicate maneuvers such as peeling membranes from the retinal surface become significantly more difficult when instruments are too flexible causing imprecision of movements.

What is needed is an instrument design that accommodates increasingly small diameters, and still provides precise control without unwanted flexing.

OVERVIEW

The present instruments, and related methods provide means for diminishing the "play" in very small and flexible instruments, such as instruments for ophthalmological surgery. Embodiments described include designs where characteristics such as stiffness can be adjusted by a surgeon. Embodiments described also include adjustments so access is possible to all parts of the vitreous cavity. Embodiments described also include an adjustment mechanism where a level of support of a small diameter instrument can be varied, yet a number of supply lines remain located in a central part of a base unit, and the support frame is contained within a substantially continuous gripping surface of the base unit.

To better illustrate the instruments, and related methods disclosed herein, a non-limiting list of examples is now provided:

In Example 1, an ophthalmologic instrument includes a base unit having a lateral gripping surface, a small diameter instrument extending from the base unit, the small diameter instrument having a length, one or more supply lines routed through an interior of the base unit to the small diameter instrument, a support frame slidably coupled to the small diameter instrument along the length, and an adjustment mechanism for the support frame, to provide two or more different levels of lateral support to the small diameter instrument, wherein the support fame is spaced apart from the one or more supply lines, and contained within the lateral gripping surface.

In Example 2, the ophthalmologic instrument of Example 1 is optionally configured such that the adjustment mechanism includes one or more rods that slide within holes in the base unit.

In Example 3, the ophthalmologic instrument of any one or any combination of Examples 1-2 is optionally configured such that the adjustment mechanism includes a scale on a side of a rod to indicate the different levels of lateral support.

In Example 4, the ophthalmologic instrument of any one or any combination of Examples 1-3 is optionally configured such that the adjustment mechanism includes a threaded knob to adjust the levels of lateral support.

In Example 5, the ophthalmologic instrument of any one or any combination of Examples 1-4 is optionally configured such that the adjustment mechanism includes a flexible cable between the threaded knob and the one or more rods.

In Example 6, the ophthalmologic instrument of any one or any combination of Examples 1-5 is optionally configured such that the one or more supply lines includes a supply line chosen from a group consisting of fiber optics, media infusion, suction, and drug, or other fluid delivery.

In Example 7, the ophthalmologic instrument of any one or any combination of Examples 1-6 is optionally configured such that the one or more supply lines includes a supply line to deliver an instrument chosen from a group consisting of cutting tools, forceps, and scissors.

In Example 8, the ophthalmologic instrument of any one or any combination of Examples 1-7 is optionally configured such that the support frame includes a cylinder that fits closely around the small diameter instrument.

In Example 9, the ophthalmologic instrument of any one or any combination of Examples 1-8 is optionally configured such that the small diameter instrument is approximately 23 gauge or smaller in diameter.

In Example 10, the ophthalmologic instrument of any one or any combination of Examples 1-9 is optionally configured such that the small diameter instrument is approximately 25 gauge in diameter.

In Example 11, the ophthalmologic instrument of any one or any combination of Examples 1-10 is optionally configured such that the small diameter instrument is approximately 27 gauge in diameter.

In Example 12, a method includes gripping a substantially continuous lateral surface of a base unit of an instrument, adjusting a support device along a length of a hollow instrument having a diameter of 23 gauge or less to select a level of lateral support, and applying lateral force with the small diameter instrument, wherein the support device enhances lateral stiffness of the small diameter instrument.

In Example 13, the method of Example 12 is optionally provided such that adjusting the support device along the length of the hollow instrument having a diameter of 23 gauge or less includes adjusting a support device along a length of a hollow instrument having a diameter of approximately 25 gauge.

These and other examples and features of the instruments, and related methods will be set forth in part in the following detailed description. This overview is intended to provide non-limiting examples of the present subject matter—it is not intended to provide an exclusive or exhaustive explanation. The detailed description below is included to provide further information about the present instruments, and methods.

BRIEF DESCRIPTION OF THE DRAWINGS

FIG. 1 shows a side view of an instrument according to an embodiment of the invention.

FIG. 2 shows a top view of the instrument from FIG. 1, according to an embodiment of the invention.

DETAILED DESCRIPTION

Figure 3:
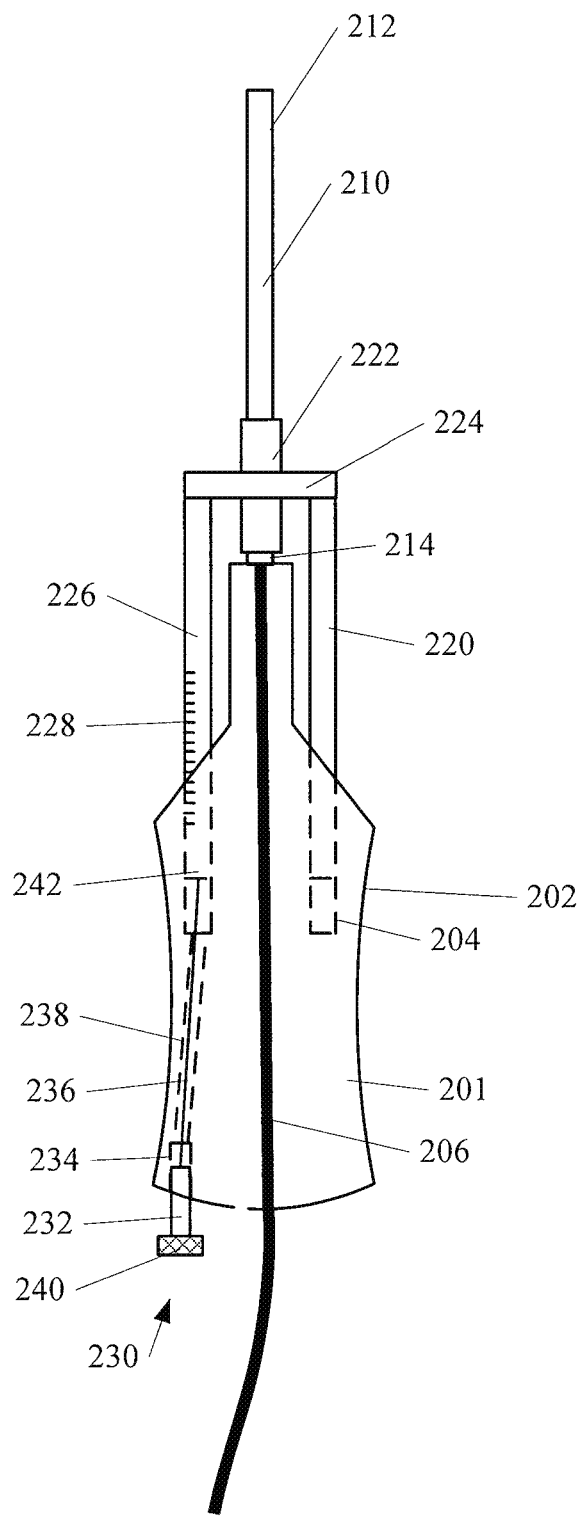
FIG. 3 shows another instrument according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an instrument 100 including a small diameter instrument 110, and a support device 120. The small diameter instrument 110 includes a distal end 112 and a proximal end 114. In one example, the small diameter instrument 110 includes a hollow tube. In one example, the small diameter instrument 110 has a diameter smaller than 20 gauge. In one example, the small diameter instrument 110 has a diameter equal to, or smaller than 23 gauge. In one example, the small diameter instrument 110 has a diameter of approximately 25 gauge.

The small diameter instrument 110 is shown extending from a base unit 101. The base unit 101 includes a lateral gripping surface 102. During a procedure, it is desirable to have the gripping surface 102 free from protrusions, or controls that may interfere with a surgeon's grip of the base unit 101. In one example, the base unit 101 is configured to be the same size and shape of a base unit in existing ophthalmological devices. It is desirable to make the base unit 101 of the present disclosure move and feel the same as existing base units, with added features, such as adjustable support.

One or more supply lines 106 are shown extending into the base unit 101 and routed through an interior of the base unit 101. In one example, one or more of the supply lines 106 includes a fiber optic supply line, such as general illumination, or a laser for drug activation, cauterization, ablation, etc. In one example, one or more of the supply lines 106 includes a passage for infusion of a media such as liquid, gas, or supply of a drug, or a passage for suction of material. In one example, one or more of the supply lines 106 includes an introducer for an instrument such as a cutting tool (e.g. scissors, blade, etc.) or other tools such as forceps, probes, etc.

In one example, it is desirable to route supply lines through approximately a center of the base unit 101 for ease of manufacture, and ease of use. Configurations described below provide adjustable properties of the instrument 100 to the surgeon without affecting location of the supply lines 106, or protruding outside of the gripping surface 102.

The small diameter instrument 110 and the support device 120 are adjustable relative to each other, allowing the surgeon to selectively provide support at different locations along a length of the small diameter instrument 110. Although "gauge" is used to define a size of the small diameter instrument, the invention is not limited to circular cross section instruments. When referring to non-circular small diameter instruments, an average diameter can be used to define a gauge.

In one example, a support device 120 of adequate stiffness is positioned along the shaft of the small diameter instrument 110 (25 gauge or the like). The support device 120 stabilizes the instrument so the surgeon using it has a greater sense of security regarding the position of the tip inside the eye. The support device 120 is adjustable so that the full length of the small diameter instrument 110 can be selectively inserted into the eye for posterior work. Posterior work typically requires minimal twisting motion by the surgeon, therefore a lower need for stabilization.

For a procedure that will benefit from more support, such as a peripheral vitrectomy, the support device 120 can be moved down the shaft of the small diameter instrument 110 to provide increased support. With the support device 120 moved closer to the distal end 112, less play is present at the distal end 112 of the small diameter instrument 110 when the eye is twisted and turned by the surgeon.

In one example, the support device 120 design includes a sliding portion 122 having a close tolerance fit with the small diameter instrument 110, to allow adjustment of support, while minimizing lateral motion of the small diameter instrument 110 within the sliding portion 122. In one example, a 20 gauge cylinder is used as a sliding portion 122. The sliding portion 122 may be constructed of a strong material such as stainless steel, to go around the small diameter instrument 110. The sliding portion 122 is attached to an adjustment mechanism, including one or more rods 126 that runs parallel to the small diameter instrument 110. In one example the sliding portion 122 is attached to the rods 126 using a coupling member 124. FIG. 1 shows the rods 126 slidably moving within holes 104 in the base unit 101. A control 130, coupled to the one or more rods 126 is pushed or pulled to move the sliding portion 122 along the length of the small diameter instrument 110 to adjust a level of lateral support.

In one example, a scale 128 such as gradated lines, or other indicia are included to indicate a relative position of the sliding portion 122 with respect to the length of the small diameter instrument 110. Examples that include the scale 128 provide an indication of the different levels of lateral support provided to the small diameter instrument 110.

In one example the one or more rods 126 are interference toleranced within the holes 104 to provide a level of friction that holds the support device 120 in a selected position with respect to the small diameter instrument 110. The friction provided by the interference tolerance is high enough to hold the support device 120 in place, once a level of support is selected, yet the level of friction is low enough, such that the surgeon can overcome the friction to make subsequent support adjustments.

In one example, the adjustment mechanism includes a positioning system 108, such as mating detents, ratchets, or the like provide a selection of the level of support by location of the support device 120 with respect to the small diameter instrument 110. Systems such as detents or ratchets, etc. provide tactile feedback to the surgeon, that along with the scale 128 are easy to operate and know when an adjustment has been made.

FIG. 2 shows an end view of the instrument 100 from FIG. 1. The small diameter instrument 110, with the sliding portion 122 is shown in approximately the center of the base unit 101. The rods 126 are shown coupled to the sliding portion 122 by the coupling member 124. The example shown in FIG. 2 illustrates a solid disk shaped coupling member 124, however one of ordinary skill in the art, having the benefit of the present disclosure, will recognize that other configurations such as struts, or complex shaped coupling members 124 are within the scope of the invention.

Three approximately equally spaced rods 126 are shown in FIG. 2, although other numbers of rods 126 are within the scope of the invention. Three substantially equally spaced rods are a stable configuration, providing support on three axes for increased stability and control.

FIG. 3 shows another embodiment of an instrument 200. Only selected features of the instrument 200 are discussed in detail. In selected examples, features that are described above regarding instrument 100 can also be incorporated into instrument 200. In FIG. 3, a small diameter instrument 210 and a support device 220 are shown. The small diameter instrument 210 is shown extending from a base unit 201. The base unit 101 includes a lateral gripping surface 202.

The small diameter instrument 210 includes a distal end 212 and a proximal end 214. Similar to the instrument 100 from FIGS. 1 and 2, in one example, the small diameter instrument 210 includes a hollow tube. In one example, the small diameter instrument 210 has a diameter smaller than 20 gauge. In one example, the small diameter instrument 210 has a diameter equal to, or smaller than 23 gauge. In one example, the small diameter instrument 210 has a diameter of approximately 25 gauge.

The support device 220 of the instrument 200 in FIG. 3 includes a sliding portion 222 having a close tolerance fit with the small diameter instrument 210, to allow adjustment of support, while minimizing lateral motion of the small diameter instrument 210 within the sliding portion 222. The sliding portion 222 is attached to an adjustment mechanism, including one or more rods 226 that runs parallel to the small diameter instrument 210. In one example the sliding portion 222 is attached to the rods 226 using a coupling member 224. FIG. 3 shows the rods 226 slidably moving within holes 204 in the base unit 201.

In the example of FIG. 3, the rods 226 do not extend all the way through the base unit 201. Ad adjustment mechanism 230 is shown, including a knob 240 that is coupled to the one or more rods 226 to move the sliding portion 222 along the length of the small diameter instrument 210 to adjust a level of lateral support. FIG. 3 shows a threaded portion 232 of the knob 240 that moves within a mating thread pocket 234, and provides precise control of the position of the sliding portion 222 along the length of the small diameter instrument 210. A cable 236, or other connection is provided between the threaded portion 232 and one or more rods 226. Use of a flexible connection such as a cable 236 allows the knob 240 to be offset laterally from the rod 226, as shown in FIG. 3.

When the knob 240 is rotated a desired amount, the cable 236 is moved within a passage 238 and in turn, actuates the rod 226. In one example, the threaded portion 232 provides 10 mm of available travel which translates through the cable 236 and the rod 226 to a position of the sliding portion 222 along the length of the small diameter instrument 210. In one example, a bearing, or other rotation joint is included in the linkage between the knob 240 and the sliding portion 222. In one example the cable 236 is coupled at location 242 in such as way as to push and pull the rod, while a bearing or other rotation joint allows the cable to rotate with respect to the rod 226, to permit adjustment of the sliding portion 222 along the length of the small diameter instrument 210.

As in the instrument 100 of FIGS. 1 and 2, in one example, a scale 228 such as gradated lines, or other indicia are included to indicate a relative position of the sliding portion 222 with respect to the length of the small diameter instrument 210. In one example, three approximately equally spaced rods 226 are used in the support device 220, although other numbers of rods 226 are within the scope of the invention. Three substantially equally spaced rods are a stable configuration, providing support on three axes for increased stability and control.

Both example instruments 100 and 200 illustrate an adjustment mechanism where a level of support of the small diameter instrument can be varied, yet the number of supply lines remain located in a central part of the base unit, and the support frame is contained within a substantially continuous gripping surface of the base unit. No adjustment controls protrude through the substantially continuous gripping surface.

Figure 4:
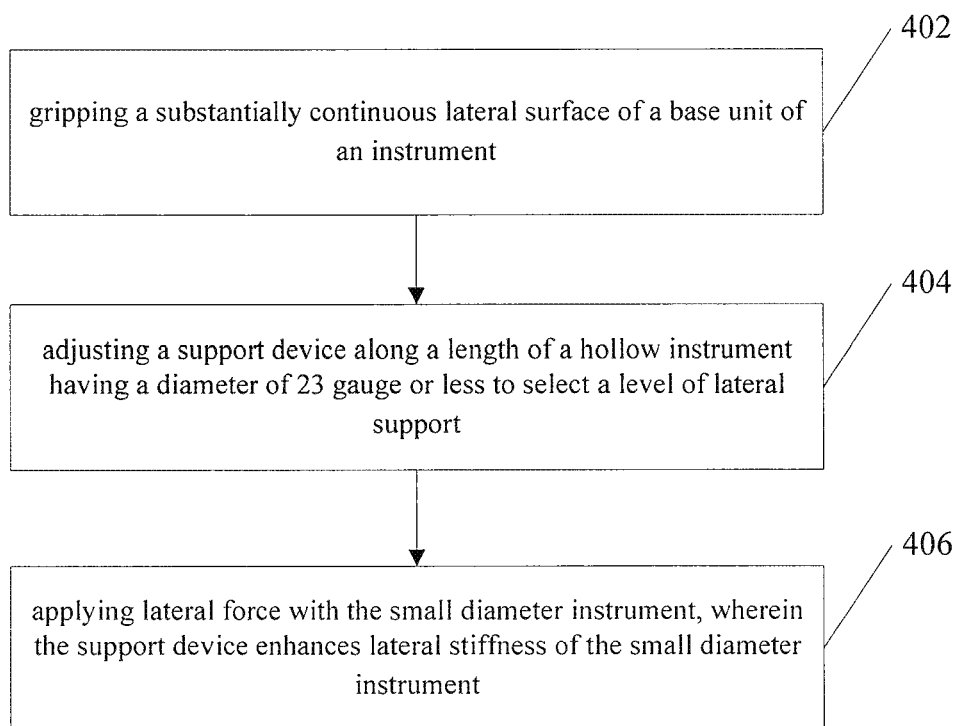
FIG. 4 shows a method of using an instrument according to an embodiment of the invention.

FIG. 4 shows a flow chart of an example method of operating a support device, such as a support device described in examples above. Operation 402 describes gripping a substantially continuous lateral surface of a base unit of an instrument. Operation 404 describes adjusting a support device along a length of a hollow instrument having a diameter of 23 gauge or less to select a level of lateral support. Operation 404 describes applying lateral force with the small diameter instrument, wherein the support device enhances lateral stiffness of the small diameter instrument.

Instruments are shown which diminish the "play" in very small and flexible instruments, such as instruments for vitreous surgery. Embodiment described above include designs where characteristics such as stiffness can be adjusted by the surgeon. Embodiments described above also include adjustments so access is possible to all parts of the vitreous cavity. Embodiments as shown above provide features to make surgical procedures safer. Embodiments described above also increase the variety of cases for which small, more flexible instruments can be used. Although vitreous surgery is discussed above as an example procedure, embodiments of the invention described above and in the following claims are not so limited. Other surgical procedures will also benefit from the advantages that these device configurations provide.

While a number of advantages of embodiments described herein are listed above, the list is not exhaustive. Other advantages of embodiments described above will be apparent to one of ordinary skill in the art, having read the present disclosure. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. An ophthalmologic instrument, comprising:
a base unit having an outer surface lateral to a longitudinal axis, with no protrusions or controls on the outer surface lateral to the longitudinal axis of the base unit;
a small diameter instrument fixed in relation to the base unit, and extending from the base unit, the small diameter instrument having a length;
a support frame slidably coupled to the small diameter instrument along the length;
an adjustment mechanism for the support frame, to provide two or more different levels of lateral support to the small diameter instrument, wherein the adjustment mechanism is located on a surface other than the outer surface lateral to the longitudinal axis of the base unit; and
wherein the support frame is spaced laterally apart from the small diameter instrument, and contained within the outer surface lateral to the longitudinal axis.

2. The ophthalmologic instrument of claim 1, wherein the adjustment mechanism includes one or more rods that slide within holes in the base unit.

3. The ophthalmologic instrument of claim 1, wherein the adjustment mechanism includes a scale on a side of a rod to indicate the different levels of lateral support.

4. The ophthalmologic instrument of claim 1, wherein the adjustment mechanism includes a threaded knob that moves within a threaded mating pocket on the base unit to adjust the different levels of lateral support.

5. The ophthalmologic instrument of claim 4, wherein the adjustment mechanism includes a flexible cable between the threaded knob and the one or more rods.

6. The ophthalmologic instrument of claim 1, wherein the small diameter instrument includes a fiber optic instrument.

7. The ophthalmologic instrument of claim 1, wherein the small diameter instrument includes an infusion cannula.

8. The ophthalmologic instrument of claim 1, wherein the small diameter instrument includes a cutting tool.

9. The ophthalmologic instrument of claim 1, wherein the small diameter instrument includes a forceps.

10. The ophthalmologic instrument of claim 1, wherein the small diameter instrument includes a probe.

11. The ophthalmologic instrument of claim 1, wherein the support frame includes a cylinder that fits closely around the small diameter instrument.

12. The ophthalmologic instrument of claim 1, wherein the small diameter instrument is approximately 23 gauge or smaller in diameter.

13. The ophthalmologic instrument of claim 1, wherein the small diameter instrument is approximately 2.5 gauge in diameter.

14. The ophthalmologic instrument of claim 1, wherein the small diameter instrument is approximately 27 gauge in diameter.

15. An ophthalmologic instrument, comprising:
a base unit having an outer surface lateral to a longitudinal axis, with no protrusions or controls on the outer surface lateral to the longitudinal axis of the base unit;
a small diameter instrument fixed in relation to the base unit, and extending from the base unit, the small diameter instrument having a length;
a support frame slidably coupled to the small diameter instrument along the length;
an adjustment mechanism for the support frame, including a plurality of rods that extend both proximally and distally through the base unit, to provide two or more different levels of lateral support to the small diameter instrument, wherein the adjustment mechanism is located on a surface other than the outer surface lateral to the longitudinal axis of the base unit; and
wherein the support frame is spaced apart from the small diameter instrument, and contained within the outer surface lateral to the longitudinal axis.

16. The ophthalmologic instrument of claim 15, wherein the adjustment mechanism includes three or more rods that slide within holes in the base unit, wherein the three or more rods form a stable configuration providing support on three axes for stability and control.

17. The ophthalmologic instrument of claim 15, wherein the outer surface lateral to the longitudinal axis includes a concave surface to facilitate gripping.

18. The ophthalmologic instrument of claim 15, wherein the small diameter instrument includes a fiber optic instrument.

19. The ophthalmologic instrument of claim 15, wherein the small diameter instrument includes an infusion cannula.

20. The ophthalmologic instrument of claim 15, wherein the small diameter instrument includes a cutting tool.

21. The ophthalmologic instrument of claim 15, wherein the small diameter instrument includes a forceps.

22. The ophthalmologic instrument of claim 15, wherein the small diameter instrument includes a probe.

* * * * *